United States Patent
Noh et al.

(10) Patent No.: US 12,087,323 B2
(45) Date of Patent: Sep. 10, 2024

(54) DEVICE AND METHOD FOR VOICE-BASED TRAUMA SCREENING USING DEEP-LEARNING

(71) Applicant: EMOCOG Co., Ltd., Seoul (KR)

(72) Inventors: Yoo Hun Noh, Yangju-si (KR); Eui Chul Lee, Seoul (KR); Na Hye Kim, Ansan-si (KR); So Eui Kim, Seoul (KR); Ji Won Mok, Siheung-si (KR); Su Gyeong Yu, Seoul (KR); Na Yeon Han, Seoul (KR)

(73) Assignee: EMOCOG CO., LTD., Seoul (KR)

( * ) Notice: Subject to any disclaimer, the term of this patent is extended or adjusted under 35 U.S.C. 154(b) by 322 days.

(21) Appl. No.: 17/455,110

(22) Filed: Nov. 16, 2021

(65) Prior Publication Data
US 2022/0157332 A1 May 19, 2022

(30) Foreign Application Priority Data

Nov. 16, 2020 (KR) .................. 10-2020-0152939
Oct. 6, 2021 (KR) .................. 10-2021-0132219

(51) Int. Cl.
*G10L 25/63* (2013.01)
*A61B 5/00* (2006.01)
(Continued)

(52) U.S. Cl.
CPC .............. *G10L 25/63* (2013.01); *A61B 5/165* (2013.01); *A61B 5/4803* (2013.01); *G06N 20/00* (2019.01);
(Continued)

(58) Field of Classification Search
CPC ......... G10L 25/63; G10L 15/22; G10L 21/12; G10L 25/18; G06N 20/00; A61B 5/165; A61B 5/4803
See application file for complete search history.

(56) References Cited

U.S. PATENT DOCUMENTS

2019/0348066 A1\* 11/2019 Funakoshi .............. G10L 21/06
2019/0385711 A1\* 12/2019 Shriberg ................. A61B 5/164
2021/0064928 A1\* 3/2021 Narisetty .............. G06F 18/245

FOREIGN PATENT DOCUMENTS

KR         10-1189765 B1     10/2012
KR    10-2015-0087671 A      7/2015
(Continued)

OTHER PUBLICATIONS

Banerjee et al., "A Deep Transfer Learning Approach for Improve Post-Traumatic Stress Disorder Diagnosis," IEEE International Conference on Data Mining, 2017, 11 pages.
(Continued)

*Primary Examiner* — Fan S Tsang
*Assistant Examiner* — David Siegel
(74) *Attorney, Agent, or Firm* — Knobbe, Martens, Olson, & Bear, LLP

(57) ABSTRACT

This application relates to a device and a method for voice-based trauma screening using deep learning. The device and method for voice-based trauma screening using deep learning screen for trauma through voices that may be obtained in a non-contact manner without limitations of space or situation. In one aspect, the device includes a memory configured to store at least one program and a processor configured to perform an operation by executing the at least one program. The processor can obtain voice data, pre-process the voice data, convert pre-processed voice data into image data, and input the image data to a deep learning model and obtain a trauma result value as an output value of the deep learning model.

7 Claims, 8 Drawing Sheets

(51) Int. Cl.
- *A61B 5/16* (2006.01)
- *G06N 20/00* (2019.01)
- *G10L 15/22* (2006.01)
- *G10L 21/12* (2013.01)
- *G10L 25/18* (2013.01)

(52) U.S. Cl.
CPC .............. *G10L 15/22* (2013.01); *G10L 21/12* (2013.01); *G10L 25/18* (2013.01)

(56) References Cited

FOREIGN PATENT DOCUMENTS

| | | | |
|---|---|---|---|
| KR | 10-2019-0087353 | A | 7/2019 |
| KR | 10-2020-0075123 | A | 6/2020 |
| KR | 10-2020-0105589 | A | 9/2020 |
| KR | 10-2020-0109958 | A | 9/2020 |
| KR | 10-2020-0119388 | A | 10/2020 |
| WO | WO 2019/246239 | A1 | 12/2019 |

OTHER PUBLICATIONS

Choee et al., "CNN-based Speech Emotion Recognition using Transfer Learning," Journal of Korean Institute of Intelligent Systems, vol. 29, No. 5, pp. 339-344, Oct. 2019.

Extended European Search Report in European Patent Application No. 21208181.4 dated Apr. 7, 2022.

Kim et al., "Voice-based Emotion Classification for Screening Trauma," Journal of Next-Generation Convergence Technology Association, vol. 4, No. 5, pp. 509-515, 2020.

Lee et al., "Deep Learning based Emotion Classification using Multi Modal Bio-Signals," Journal of Korea Multimedia Society, vol. 23, No. 2, pp. 146-154, Feb. 2020.

Noroozi et al., "A Study of Language and Classifier-independent Feature Analysis for Vocal Emotion Recognition," IEEE, Arvix, arvix.og, (https://arxiv.org/pdf/1811.08935.pdf), Nov. 14, 2018, 24 pages.

Notice of Allowance in Japanese Patent Application No. 2021-186529 dated Jan. 17, 2023, 5 pages.

Notice of Allowance in Korean Patent Application No. 10-2022-0132219 dated Nov. 28, 2022, 10 pages.

Office Action in Japanese Patent Application No. 2021-186529 dated Oct. 4, 2021, 6 pages.

Office Action in Korean Patent Application No. 10-2021-0132219 dated Dec. 24, 2021, 8 pages.

Office Action in Korean Patent Application No. 10-2022-0132219 dated Jul. 18, 2022, 8 pages.

Tripathi et al., "Deep Learning based Emotion Recognition System Using Speech Features and Transcriptions," Samsung R&D Institute India—Bangalore, (https://arxiv.org/ftp/arxiv/papers/1906/1906.05681.pdf) Jun. 11, 2019, 12 pages.

\* cited by examiner

DEVICE AND METHOD FOR VOICE-BASED TRAUMA SCREENING USING DEEP-LEARNING

CROSS-REFERENCE TO RELATED APPLICATION

This application is based on and claims priority under 35 U.S.C. § 119 to Korean Patent Application No. 10-2021-0132219, filed on Oct. 6, 2021, and Korean Patent Application No. 10-2020-0152939, filed on Nov. 16, 2020 in the Korean Intellectual Property Office, the disclosure of each of which is incorporated by reference herein in its entirety.

BACKGROUND

Technical Field

One or more embodiments relate to a device and a method for voice-based trauma screening using deep learning, and more particularly, to a device and a method for voice-based trauma screening using deep learning by recognizing an emotion and estimating possibility of trauma through deep-learning of voice data.

Description of Related Technology

Today, modern people are exposed to various types of stress, from everyday events like studying and working to serious events like traffic accidents and crimes. Trauma refers to the medical term post-traumatic stress disorder (PTSD) and refers to a mental injury caused by an external traumatic event. People who experience trauma have difficulty of controlling and stabilizing their emotions. Spontaneous recovery rate is as high as 60% or more within the first year of trauma, but drops sharply thereafter. Therefore, early treatment within 1 year of experiencing trauma is very important for recovery from the trauma. For early treatment, it is essential to visit a hospital and consult with a specialist to diagnose trauma. However, diagnosis and treatment of trauma often fail due to social prejudice against mental illness or failure to recognize the trauma.

In recent years, deep learning has been used to combine engineering techniques with the medical field to aid doctors in early diagnosis. In particular, voice is widely used, because it contains emotions and intentions that are effective in recognizing a patient's emotions and may be obtained in a non-contact manner in a natural environment without the patient feeling rejection. Also, although many studies using voice for age classification and emotion recognition are being conducted, no trauma screening study using voice analysis is currently being conducted.

The background art of the present disclosure is disclosed in Korean Patent Registration No. 10-1189765.

SUMMARY

One or more embodiments include a device and a method for voice-based trauma screening using deep learning for screening for trauma in a non-contact manner by using voice that may be obtained without a sense of rejection as compared to images.

One or more embodiments include a device and a method for voice-based trauma screening using deep learning for screening for trauma by converting voice data into image data.

One or more embodiments include a device and a method for voice-based trauma screening using deep learning, in which the accuracy of recognition is improved through post-processing after recognition of an emotion of a voice through deep learning.

One or more embodiments include a device and a method for voice-based trauma screening using deep learning that is helpful in trauma diagnosis by conveniently recognizing emotions with voice only without a specific situation or space.

Additional aspects will be set forth in part in the description which follows and, in part, will be apparent from the description, or may be learned by practice of the presented embodiments of the disclosure.

According to one or more embodiments, provided is a voice-based trauma screening device utilizing deep learning.

The voice-based trauma screening device utilizing deep learning according to an embodiment of the present disclosure includes an input unit configured to obtain voice data, a pre-processor configured to edit the voice data, a converter configured to convert edited voice data into image data, a deep learning unit configured to recognize emotions by using the image data, and a determiner configured to post-process a result value from the deep learning unit.

According to one or more embodiments, provided is a voice-based trauma screening method utilizing deep learning and a computer-readable recording medium having recorded thereon the method.

According to one or more embodiments, provided are a voice-based trauma screening method utilizing deep learning according to an embodiment of the present disclosure and a recording medium having stored thereon a computer program executing the same. The voice-based trauma screening method includes obtaining voice data, pre-processing the voice data, converting the pre-processed voice data into image data, deep learning the image data, and post-processing a result of the deep learning.

BRIEF DESCRIPTION OF THE DRAWINGS

The above and other aspects, features, and advantages of certain embodiments of the disclosure will be more apparent from the following description taken in conjunction with the accompanying drawings.

DETAILED DESCRIPTION

Figure 1:
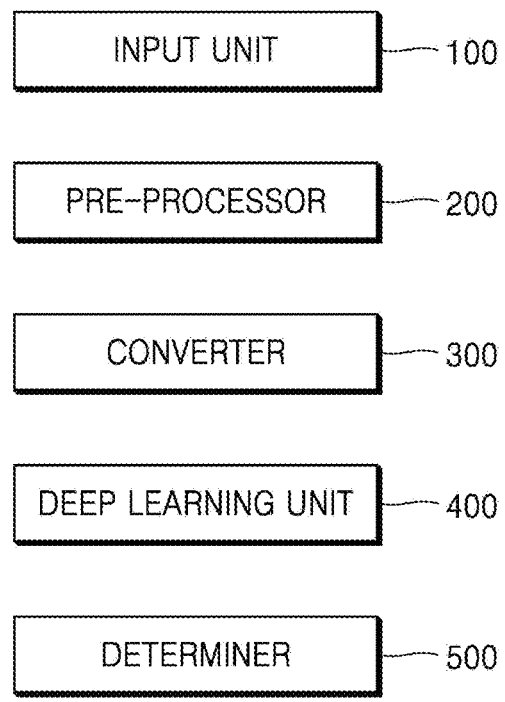
FIG. 1 is a block diagram of a voice-based trauma screening device utilizing deep learning according to an embodiment.

The present disclosure may include various embodiments and modifications, and embodiments thereof will be illustrated in the drawings and will be described herein in detail. However, this is not intended to limit the inventive concept to particular modes of practice, and it is to be appreciated that all changes, equivalents, and substitutes that do not depart from the spirit and technical scope of the inventive concept are encompassed in the present disclosure. In the following description of the present disclosure, the detailed description of known functions and configurations incorporated herein is omitted when it may make the subject matter of the present disclosure rather unclear. Also, as used herein and in the claims, the terms "a" and "an" are generally to be construed to mean "one or more" unless stated otherwise.

Hereinafter, example embodiments of the present disclosure will be described in detail with reference to the accompanying drawings. In the drawings, the same elements or elements corresponding to each other will be denoted by the same reference numerals, and repeated descriptions thereof will be omitted.

FIGS. 1 to 5 are diagrams for describing a voice-based trauma screening device utilizing deep learning according to an embodiment of the present disclosure.

FIG. 1 is a block diagram of a voice-based trauma screening device 10 utilizing deep learning according to an embodiment.

Referring to FIG. 1, the voice-based trauma screening device 10 utilizing deep learning includes an input unit 100, a pre-processor 200, a converter 300, a deep learning unit 400, and a determiner 500.

The voice-based trauma screening device 10 utilizing deep learning screens trauma in voice data. The voice-based trauma screening device 10 utilizing deep learning screens trauma rather than determining the presence of trauma, and thus a voice may be obtained in a non-contact manner under natural environment without repulsion.

The voice-based trauma screening device 10 utilizing deep learning recognizes four emotions, that is, happiness, neutrality, sadness, and fear from voice data and screens trauma. The voice-based trauma screening device 10 utilizing deep learning uses the four emotions, because many people feel a lot of fear when they are traumatized, and, as time passes after the trauma, the sadness becomes intense and is often developed into depression. In the early stages of trauma, feelings of fear, sadness, surprise, and anger are noticeable, and, as time passes, the anger is weakened and the fear and the sadness become intense. The voice-based trauma screening device 10 utilizing deep learning screens trauma under the assumption that trauma probability is high when fear and sadness are recognized from voice data and trauma probability is low when neutrality and happiness appear in voice data.

The input unit 100 receives an input of a voice and generates voice data therefrom or receives and obtains voice data.

Figure 2:
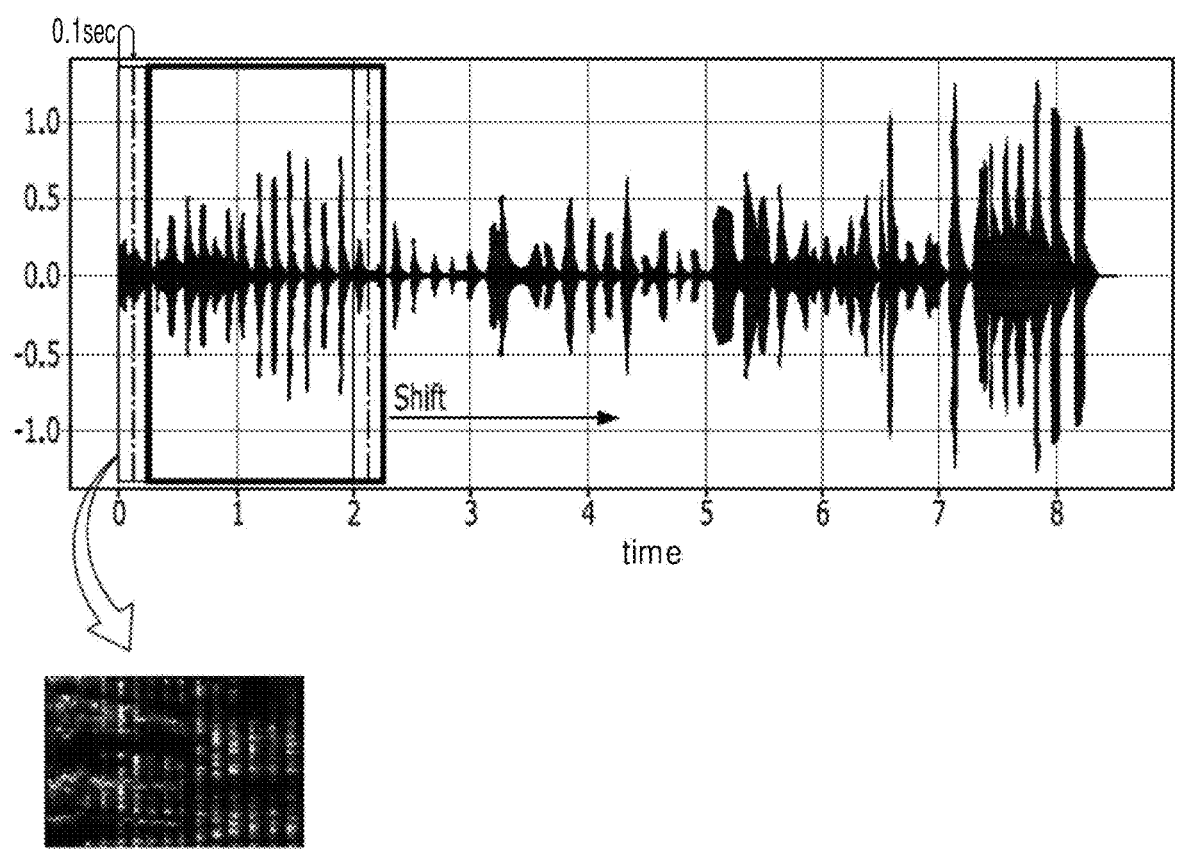
FIG. 2 is a diagram for describing a method of converting voice data into image data according to an embodiment.

FIG. 2 is a diagram for describing a method of converting voice data into image data according to an embodiment.

Referring to FIG. 2, the pre-processor 200 removes differences between lengths of data and increases the number of voice data to convert obtained voice data into image data. For example, the pre-processor 200 shifts in units of 0.1 second and edits in units of 2 seconds.

The converter 300 converts voice data into image data. In more detail, the converter 300 converts 1-dimensional voice data into 2-dimensional spectrogram image data by using a Short-Time Fourier Transform (STFT) spectrogram. For example, the converter 300 performs Fast Fourier Transform (FFT) on pre-processed voice data by specifying the number of samplings per second to 1024 and shifts image data by overlapping by 512 samples.

The converter 300 scales all image data values to be between 0 and 1 by using a min-max scaler. The min-max scaler normalizes the data to a range between 0 and 1 by using a minimum value Min and a maximum value Max.

Figure 3:
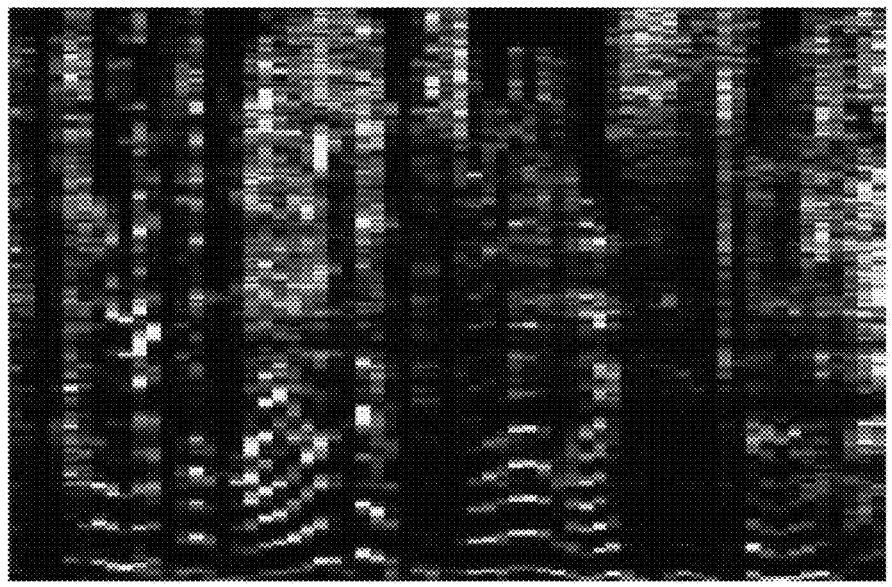
FIG. 3 is a diagram showing an example of image data according to an embodiment.

FIG. 3 is a diagram showing an example of image data according to an embodiment.

Referring to FIG. 3, a result of converting voice data into spectrogram image data by the converter 300 may be confirmed.

The deep learning unit 400 uses the spectrogram image data as an input value of a deep learning model and learns to recognize emotions.

The deep learning unit 400 learns by using a Visual Geometry Group-13 (VGG-13) model from among convolutional neural network (CNN) models. The deep learning unit 400 uses a Korean voice dataset generated by extracting voices containing six basic emotions (happiness, sadness, disgust, anger, fear, and surprise) from domestic broadcasts and movies. In the Korean voice data set, the length of each voice data is from about 2 seconds to about 11 seconds, and there are a total of 600 voice data for each emotion. The deep learning unit 400 learns by using only voice data corresponding to four emotions of fear, sadness, neutrality, and happiness from among the Korean voice data set.

Figure 4:
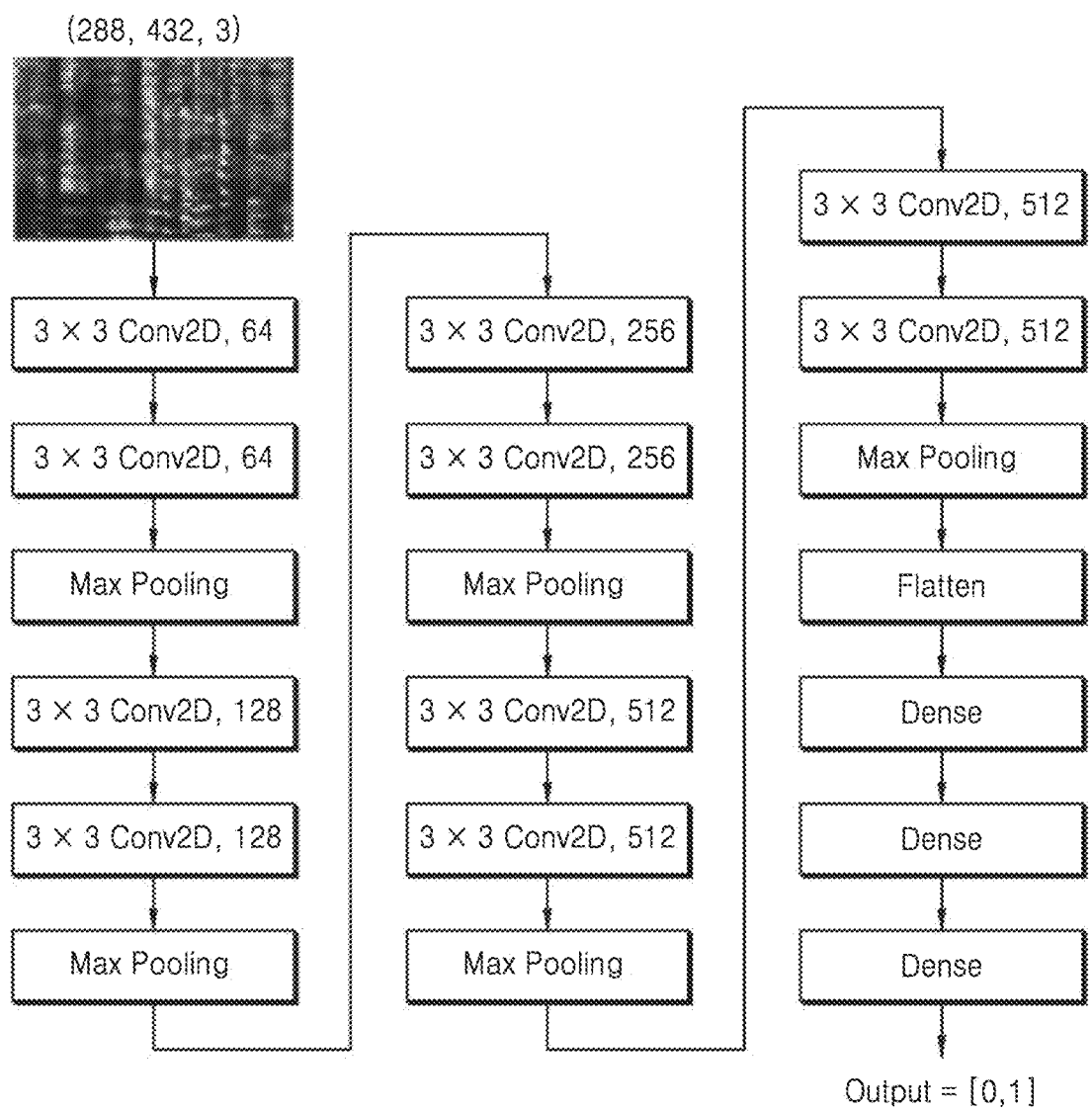
FIG. 4 is a diagram showing an example of a deep learning model according to an embodiment.

FIG. 4 is a diagram showing an example of a deep learning model according to an embodiment.

Referring to FIG. 4, the deep learning unit 400 includes ten convolutional layers Cony-layers of a 3*3 kernel, five max pooling layers, and three fully connected layers. For example, the deep learning unit 400 uses spectrogram image data having the size of 288*432*3 as an input. The deep learning unit 400 may perform (deep learning on?) a max pooling layer of a 2*2 kernel after two convolutional layers Cony-layers of a 3*3 kernel. Next, the deep learning unit 400 outputs a trauma screening value as a value of 0 or 1, which is a binary classification, through a fully connected layer. In other words, the deep learning unit 400 outputs a value corresponding to a case in which a probability of having a trauma is high or a value corresponding to a case in which a probability of not having a trauma is high through binary classification.

The determiner 500 post-processes a result from the deep learning unit 400, thereby improving the accuracy thereof. The determiner 500 improves the reliability of a final result by screening for trauma when results from the deep learning unit 400 are maintained constant for a certain period of time. For example, the determiner 500 may pre-set a window size to from 2 to 10. When results from the deep learning unit 400 are maintained at 0 or 1 in correspondence to a set window size, the determiner 500 finally screens for trauma.

Figure 5:
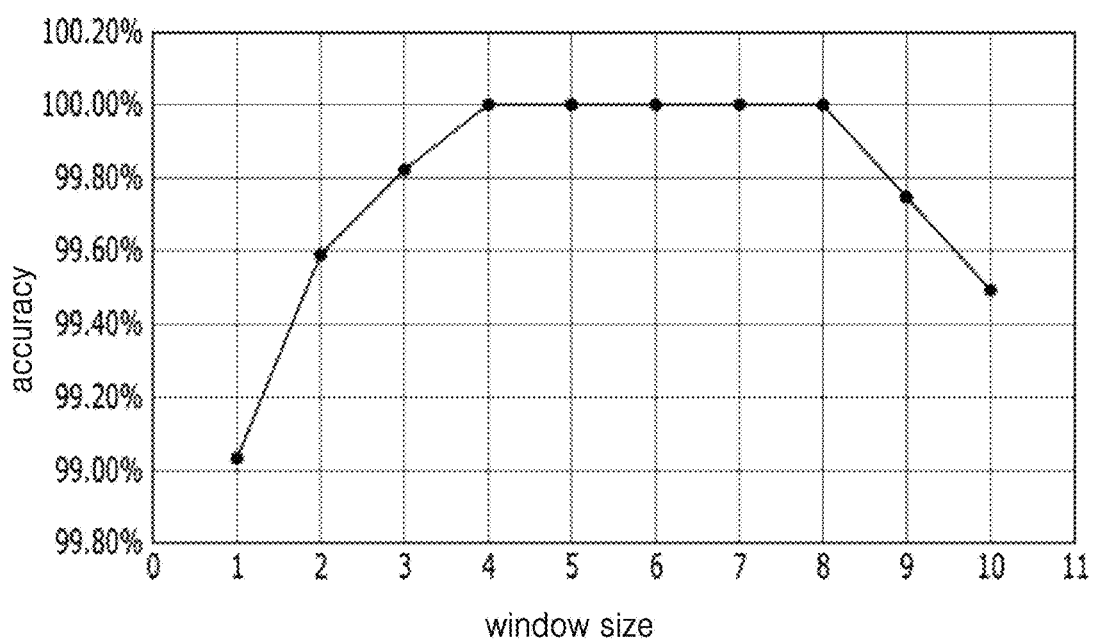
FIG. 5 is a diagram for describing a result value from a deep learning model according to a window size according to an embodiment.

FIG. 5 is a diagram for describing a result value from a deep learning model according to a window size according to an embodiment.

Referring to FIG. 5, the determiner 500 sets a window size to from 4 to 8 and extracts result values only when the result value are maintained in correspondence to a set window size. It may be confirmed that, by doing so, the accuracy of emotion recognition by the determiner 500 from voice data is 100%. A window size 1 corresponds to a case in which the determiner 500 does not perform post-processing, and the accuracy of emotion recognition is 99.03. However, it may be confirmed that, when the window size is set to from 4 to 8 and the determiner 500 performs post-processing, the accuracy of emotion recognition is 100%. In detail, in order for the voice-based trauma screening device 10 utilizing deep learning to recognize accurate emotions from voice data, voice for from 400 ms to 800 ms may be used to increase accuracy of emotion recognition, instead of voice for 100 ms. When voice data maintains the same emotion for from 400 ms to 800 ms, the voice-based trauma screening device 10 utilizing deep learning may determine that the voice represents the corresponding emotion. Therefore, the voice-based trauma screening device 10 utilizing deep learning uses only result values corresponding to window sizes from 4 to 8.

Figure 6:
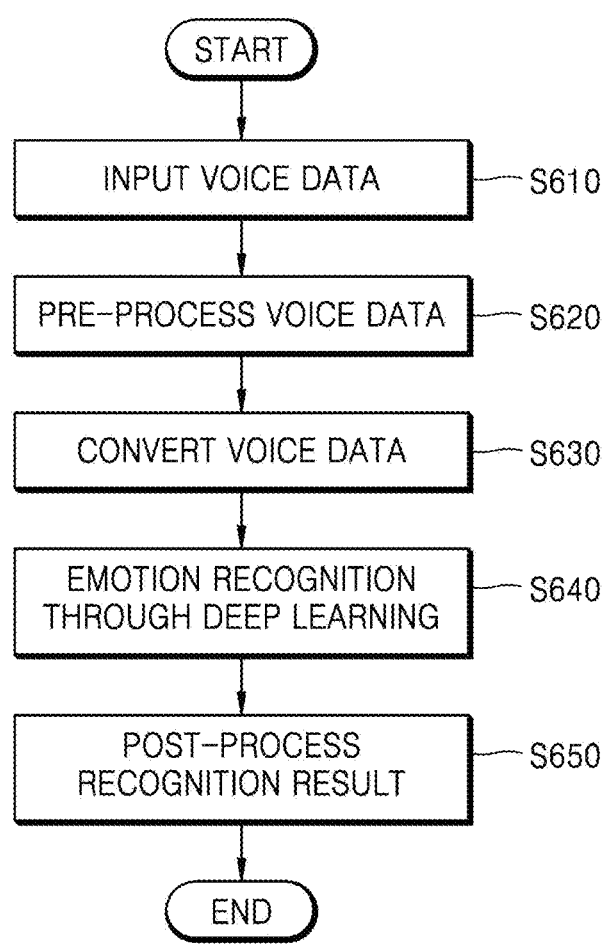
FIG. 6 is a diagram showing a voice-based trauma screening method utilizing deep learning.

FIG. 6 is a diagram showing a voice-based trauma screening method utilizing deep learning.

Each of operations described below is an operation performed by each functional unit constituting a voice-based trauma screening device utilizing deep learning. However, for conciseness and clarity of explanation of the present disclosure, it will be described below that the operations are performed by a voice-based trauma screening device utilizing deep learning.

In operation S610, the voice-based trauma screening device 10 utilizing deep learning obtains voice data needed for emotion recognition. The voice-based trauma screening device 10 utilizing deep learning directly receives a voice and generates voice data or receives and obtains voice data generated in advance.

In operation S620, the voice-based trauma screening device 10 utilizing deep learning pre-processes input voice data to be suitable for emotion recognition. The voice-based trauma screening device 10 utilizing deep learning edits the length of voice data to be the same and increases the number of voice data (augmentation). For example, the voice-based trauma screening device 10 utilizing deep learning cuts voice data in units of 2 s while shifting the voice data in units of 0.1 s.

In operation S630, the voice-based trauma screening device 10 utilizing deep learning converts pre-processed voice data into image data. In detail, the voice-based trauma screening device 10 utilizing deep learning converts 1-dimensional voice data edited in units of 2 s into 2-dimensional spectrogram image data through a Short Time Fourier Transformation (STFT). For example, the voice-based trauma screening device 10 utilizing deep learning performs Fast Fourier Transformation (FFT) on pre-processed voice data by specifying the number of samples per second as 1024 and overlaps (image data?) for 512 samples and shifts (the image data?). Next, spectrogram image data is scaled through the min-max scaler, such that the values of all result data are between 0 and 1.

In operation S640, the voice-based trauma screening device 10 utilizing deep learning deep-learns scaled spectrogram image data. The voice-based trauma screening device 10 utilizing deep learning performs emotion recognition using the Visual Geometry Group-13 (VGG-13) model from among CNN models. The deep learning model is described above with reference to FIG. 4.

In operation S650, the voice-based trauma screening device 10 utilizing deep learning post-processes result values obtained by using the deep learning model, thereby improving the accuracy of voice-based emotion recognition. Since the accuracy of voice-based emotion recognition is 100% when the window size is from 4 to 8, the voice-based trauma screening device 10 utilizing deep learning uses a result value of deep learning as a result of trauma screening only when the result value corresponds to a window size from 4 to 8.

Figure 7:
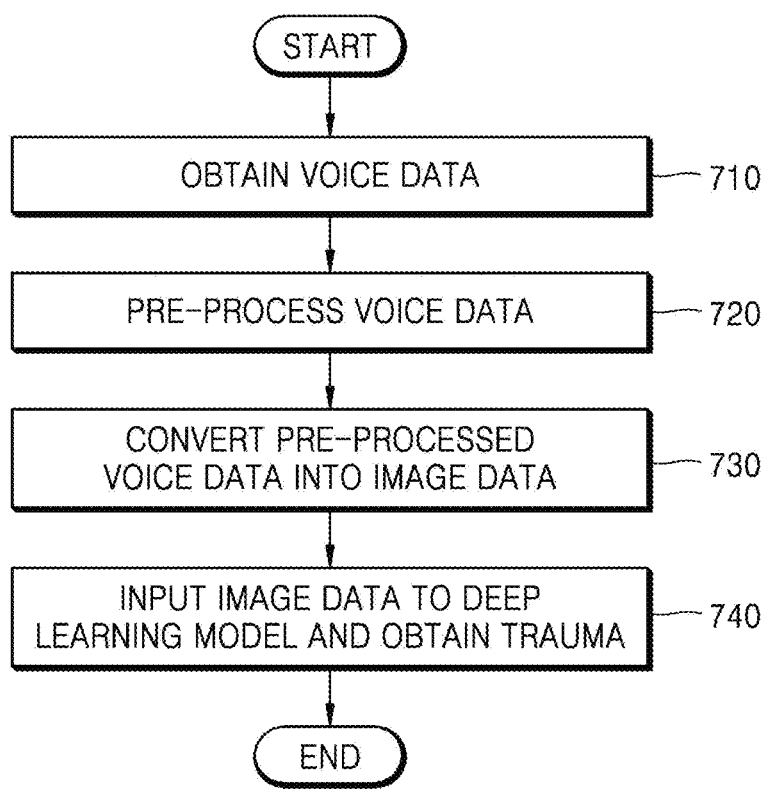
FIG. 7 is a flowchart of a voice-based trauma screening method utilizing deep learning according to an embodiment.

FIG. 7 is a flowchart of a voice-based trauma screening method utilizing deep learning according to an embodiment.

Since the method shown in FIG. 7 is related to the embodiments described above with reference to the previous drawings, descriptions given above with reference to the previous drawings may also be applied to the method of FIG. 10 even when omitted below.

Referring to FIG. 7, in operation 710, a processor may obtain voice data.

In the voice data, not only content information, but also emotions of a speaker may be reflected.

In operation 720, the processor may pre-process the voice data.

In an embodiment, the voice data may be pre-processed by shifting the voice data by a predetermined time unit, such that the voice data becomes data having a predetermined length. The processor may eliminate differences between lengths of the voice data and increase the number of voice data through a pre-processing process.

In operation 730, the processor may convert pre-processed voice data into image data.

The processor may generate 2-dimensional data by performing a Short-Time Fourier transformation on the pre-processed voice data and may utilize generated 2-dimensional data as image data.

In operation 740, the processor may input the image data to a deep learning model and obtain a trauma result value as an output value of the deep learning model.

When the trauma result value is 1, the probability that the speaker of the corresponding voice data has trauma may be high. On the contrary, when the trauma result value is 0, the probability that the speaker of the corresponding voice data has trauma may be low.

In an embodiment, the processor may input the image data to a deep learning model and obtain an emotion result value as an output value of the deep learning model. The emotion result value may be classified into a first emotion class or a second emotion class. For example, the first emotion class may include neutrality and happiness, which have low correlation with trauma, and the second emotion class may include fear, sadness, anger, and surprise, which are highly correlated with trauma, but the first emotion class and the second emotion class are not limited to the above-described examples.

In an embodiment, the processor may determine the level of trauma based on an emotion result value obtained as an output value of the deep learning model. An emotion result value may be classified into a first emotion class, a second emotion class, and a third emotion class.

For example, the first emotion class may include neutrality and happiness, which have low correlation with trauma, the second emotion class may include fear and surprise, which are highly correlated with trauma, and the third emotion class may include sadness and anger, which become prominent after a predetermined time is elapsed after trauma.

For example, when an emotion result value obtained as an output value of the deep learning model corresponds to the second emotion class, the processor may determine that trauma of the speaker of the voice data is in the early stage.

Figure 8:
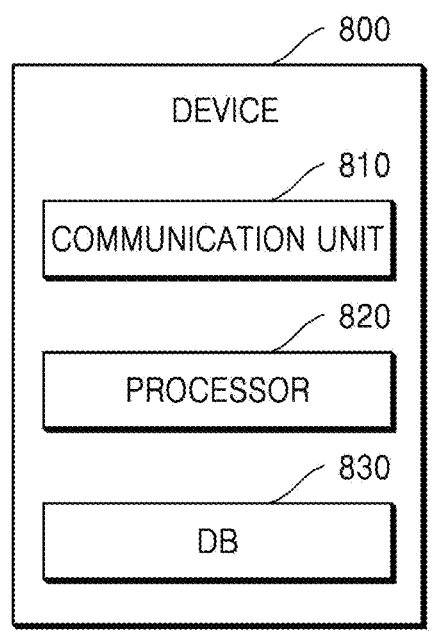
FIG. 8 is a block diagram of a device according to an embodiment.

FIG. 8 is a block diagram of a device according to an embodiment.

Referring to FIG. 8, a device 1100 may include a communication unit 810, a processor 820, and a DB 830. In the device 800 of FIG. 8, only the components related to the embodiment are shown. Therefore, one of ordinary skill in the art will understand that other general-purpose components may be further included in addition to the components shown in FIG. 8.

The communication unit 810 may include one or more components that enable wired/wireless communication with an external server or an external device. For example, the communication unit 810 may include at least one of a short-range communication unit (not shown), a mobile communication unit (not shown), and a broadcast receiving unit (not shown).

The DB 830 is hardware for storing various data processed in the device 800 and may store a program for processing and controlling the processor 820.

The DB 830 may include a random access memory (RAM) like a dynamic random access memory (DRAM) and a static random access memory (SRAM), a read-only memory (ROM), an electrically erasable programmable read-only memory EEPROM, a CD-ROM, a Blu-ray or other optical disc storage, a hard disk drive (HDD), a solid state drive (SSD), or a flash memory.

The processor 820 controls the overall operation of the device 800. For example, the processor 820 may generally control an input unit (not shown), a display (not shown), the communication unit 810, and the DB 830 by executing programs stored in the DB 830. The processor 820 may control the operation of the device 800 by executing programs stored in the DB 830.

The processor 820 may control at least some of the operations of the lane determining apparatus described above with reference to FIGS. 1 to 7.

The processor 820 may be implemented by using at least one of application specific integrated circuits (ASICs), digital signal processors (DSPs), digital signal processing devices (DSPDs), programmable logic devices (PLDs), field programmable gate arrays (FPGAs), controllers, microcontrollers, and other electrical units for performing functions.

Meanwhile, the processor 820 may include a data learning unit and a data recognition unit that perform learning and inference of a deep learning model.

The data learning unit may learn a criterion for determining a situation. The data learning unit may learn a criterion regarding which data to use to determine a predetermined situation and how to determine the situation by using data. The data learning unit may obtain data to be used for learning and apply the obtained data to a data recognition model to be described later, thereby learning a criterion for determining a situation.

The data recognition unit may determine a situation based on data. The data recognition unit may recognize a situation from predetermined data by using a learned data recognition model. The data recognition unit may determine a predetermined situation based on predetermined data by obtaining the predetermined data according to a criterion set in advance through learning and using the data recognition model by using the predetermined data as an input. Also, a result value output by the data recognition model by using the predetermined data as the input may be used to update the data recognition model.

At least one of the data learning unit and the data recognition unit may be manufactured in the form of at least one hardware chip and mounted in an electronic device. For example, at least one of the data learning unit and the data recognition unit may be manufactured in the form of a dedicated hardware chip for artificial intelligence (AI) or may be manufactured in the form of a part of an existing general-purpose processor (e.g., a CPU or an application processor) or a processor dedicated for graphics (e.g., GPU) and mounted in various electronic devices described above.

In this case, the data learning unit and the data recognition unit may be mounted in one electronic device (e.g., a lane determining device) or may be mounted in separate electronic devices. For example, one of the data learning unit and the data recognition unit may be included in a lane determining device, and the other one may be included in a server. Also, the data learning unit and the data recognition unit may communicate with each other via a wire or wirelessly to provide model information established by the data learning unit to the data recognition unit or provide data input to the data recognition unit to the data learning unit as additional training data.

According to an embodiment of the present disclosure, a device and a method for voice-based trauma screening using deep learning may screen for trauma through voices that may be obtained in a non-contact manner without limitations of space or situation.

According to an embodiment of the present disclosure, the accuracy of trauma screening may be improved by converting voice data into image data, recognizing emotions through deep learning, and post-processing a result of the deep learning.

Embodiments according to the present disclosure may be implemented in the form of a computer program that may be executed through various components on a computer, and such a computer program may be recorded in a computer-readable recording medium. In this case, the recording medium may include a magnetic medium like a hard disk, a floppy disk, and a magnetic tape, an optical recording medium like a CD-ROM and a DVD, a magneto-optical medium like a floptical disk, and a hardware device specially configured to store and execute program instructions like a ROM, a RAM, and a flash memory.

Meanwhile, the computer program may be specially designed and configured for the present disclosure or may be known and made available to one of ordinary skill in the computer software field. Examples of program commands include machine language code such as code generated by a compiler, as well as high-level language code that may be executed by a computer using an interpreter or the like.

According to an embodiment, methods according to various embodiments of the present disclosure may be included and provided in computer program products. Computer program products may be traded between sellers and buyers as commodities. Computer program products may be distributed in the form of a machine-readable recording medium (e.g., a compact disc read-only memory (CD-ROM)), distributed on-line via an application store (e.g., PlayStore™), or directly between two user devices. In the case of online distribution, at least a portion of a computer program product may be temporarily stored or temporarily generated in a machine-readable recording medium like a memory of a server of a manufacturer, a memory of a server of an application store, or a memory of a relay server.

The operations constituting the method according to the present disclosure may be performed in an appropriate order, unless explicitly stated or stated otherwise. The present disclosure is not necessarily limited to the order in which the operations are described. The use of any and all examples, or exemplary language (e.g., "such as") provided herein, is intended merely to better illuminate the disclosure and does not pose a limitation on the scope of the present disclosure unless otherwise claimed. Also, one of ordinary skill in the art will understand that various modifications, combinations, and changes may be made in accordance with design conditions and factors within the scope of the appended claims or their equivalents.

Therefore, the technical concept of the present disclosure should not be limited to particular modes of practice, and it is to be appreciated that all changes, equivalents, and substitutes that do not depart from the spirit and technical scope of the present disclosure are encompassed in the present disclosure.

What is claimed is:

1. A voice-based trauma screening device utilizing deep learning comprising:
a memory configured to store at least one program; and
a processor configured to perform an operation by executing the at least one program, the processor configured to:
obtain voice data,
pre-process the voice data,
convert pre-processed voice data into image data,
input the image data to a deep learning model and obtain a trauma result value as an output value of the deep learning model, the output value comprising an emotion result value corresponding to a first emotion class, a second emotion class, or a third emotion class,
obtain the emotion result value only in response to the emotion result value being maintained in correspondence to a set window size,
determine existence of trauma of a speaker of the voice data in response to the obtained emotion result value corresponding to the second emotion class or the third emotion class,
determine that the trauma of the speaker of the voice data is in an early stage in response to the obtained emotion result value corresponding to the second emotion class, and
determine that the trauma of the speaker of the voice data is beyond the early stage in response to the obtained emotion result value corresponding to the third emotion class.

2. The voice-based trauma screening device utilizing deep learning of claim 1, wherein the processor is configured to pre-process the voice data by shifting the voice data by a predetermined time unit such that the voice data becomes data having a predetermined length.

3. The voice-based trauma screening device utilizing deep learning of claim 1, wherein the processor is configured to:
generate 2-dimensional data by performing Short-Time Fourier Transformation on the pre-processed voice data, and
input the 2-dimensional data to input to the deep learning model as image data.

4. The voice-based trauma screening device utilizing deep learning of claim 1, wherein the first emotion class includes one or more first mental states of the speaker having low correlation with trauma, wherein the second emotion class includes one or more second mental states of the speaker being highly correlated with trauma, and wherein the third emotion class includes one or more third mental states of the speaker configured to become prominent after a predetermined time is elapsed after trauma.

5. The voice-based trauma screening device utilizing deep learning of claim 4, wherein the one or more first mental states of the speaker comprise neutrality and happiness, wherein the one or more second mental states of the speaker comprise fear and surprise, and wherein the one or more third mental states of the speaker comprise sadness and anger.

6. A voice-based trauma screening method utilizing deep learning comprising:
obtaining, at a processor, voice data;
pre-processing, at the processor, the voice data;
converting, at the processor, pre-processed voice data into image data;
inputting, at the processor, the image data to a deep learning model and obtaining a trauma result value as an output value of the deep learning model, the output value comprising an emotion result value corresponding to a first emotion class, a second emotion class, or a third emotion class;
obtaining the emotion result value only in response to the emotion result value being maintained in correspondence to a set window size;
determining existence of trauma of a speaker of the voice data in response to the obtained emotion result value corresponding to the second emotion class or the third emotion class;
determining that the trauma of the speaker of the voice data is in an early stage in response to the obtained emotion result value corresponding to the second emotion class; and
determining that trauma of the speaker of the voice data is beyond the early stage in response to the obtained emotion result value corresponding to the third emotion class.

7. A non-transitory computer-readable recording medium storing instructions, when executed by one or more processors, to perform a voice-based trauma screening method utilizing deep learning, the method comprising:
obtaining voice data;
pre-processing the voice data;
converting pre-processed voice data into image data;
inputting the image data to a deep learning model and obtaining a trauma result value as an output value of the deep learning model, the output value comprising an emotion result value corresponding to a first emotion class, a second emotion class, or a third emotion class;
obtaining the emotion result value only in response to the emotion result value being maintained in correspondence to a set window size;
determining existence of trauma of a speaker of the voice data in response to the obtained emotion result value corresponding to the second emotion class or the third emotion class;
determining that the trauma of the speaker of the voice data is in an early stage in response to the obtained emotion result value corresponding to the second emotion class; and
determining that trauma of the speaker of the voice data is beyond the early stage in response to the obtained emotion result value corresponding to the third emotion class.

* * * * *